United States Patent [19]

Neuss et al.

[11] Patent Number: 5,364,949
[45] Date of Patent: Nov. 15, 1994

[54] PROCESS FOR THE PRODUCTION OF BRANCHED FATTY ACIDS AND ESTERS THEREOF

[75] Inventors: Michael Neuss, Cologne; Horst Eierdanz, Hilden, both of Germany

[73] Assignee: Henkel Kommanditgesellschaft auf Aktien, Duesseldorf, Germany

[21] Appl. No.: 927,421
[22] PCT Filed: Mar. 15, 1991
[86] PCT No.: PCT/EP91/00496
 § 371 Date: Nov. 19, 1992
 § 102(e) Date: Nov. 19, 1992
[87] PCT Pub. No.: WO91/14670
 PCT Pub. Date: Mar. 15, 1991

[30] Foreign Application Priority Data

Mar. 24, 1990 [DE] Germany ............... 4009505

[51] Int. Cl.$^5$ ................................ C11C 3/06
[52] U.S. Cl. .................... 554/161; 554/162; 554/163
[58] Field of Search ........... 554/162, 163, 26, 27, 554/161

[56] References Cited

U.S. PATENT DOCUMENTS

| | | |
|---|---|---|
| 2,361,018 | 10/1944 | Gerhart .................. 260/23 |
| 2,623,890 | 12/1952 | Verley ................... 554/27 |
| 2,812,342 | 11/1957 | Peters ................... 554/157 |
| 3,299,110 | 1/1967 | Pine ..................... 554/162 |
| 3,873,585 | 3/1975 | Sturwold et al. ......... 260/407 |
| 4,014,910 | 3/1977 | de Klein ................ 260/413 |
| 4,371,469 | 2/1983 | Foglia et al. ........... 260/405.6 |
| 4,465,852 | 8/1993 | Sato .................... 560/247 |
| 4,822,911 | 4/1989 | Fried ................... 560/205 |
| 5,114,624 | 5/1992 | Fried ................... 554/162 |

OTHER PUBLICATIONS

Soap/Cosm./Chem. Spec., 1987, pp. 52–56.
J. Am. Oil Chem. Soc., 56, 1979, pp. 782–785.
Rev. Fr. Corps Gras, 33, pp. 431–435, 1986.
Fette, Seifen, Anstrichm, 63, 1961, pp. 633–635.
Fat. Sci. Techn., 90, 1988, pp. 1–5.
Fette, Seifen, Anstrichm, 65, 1963, pp. 105–108.
J. Chem. Soc., Chem. Comm., 7, 1974, p. 251.
JP 53/34708, Abstract only, Mar. 31, 1978.

*Primary Examiner*—Jose' G. Dees
*Assistant Examiner*—Samuel Barts
*Attorney, Agent, or Firm*—Ernest G. Szoke; Wayne C. Jaeschke; Henry E. Millson, Jr.

[57] ABSTRACT

Process for the production of branched fatty acids and their esters comprising reacting unsaturated fatty acids or esters thereof with aliphatic nonactivated olefins in the presence of layer silicates and active carbon.

20 Claims, No Drawings

PROCESS FOR THE PRODUCTION OF BRANCHED FATTY ACIDS AND ESTERS THEREOF

This invention relates to a process for the production of branched fatty acids and esters thereof by reaction of unsaturated fatty acids and esters thereof with aliphatic, non-activated olefins in the presence of layer silicates and active carbon.

Branched fatty acids are distinguished from linear fatty acids by lower pour points, lower volatility, better oxidation stability, higher wetting power and easier compoundability. Accordingly, they are important raw materials for the production of surface-active agents, for example surfactants, lubricants, rolling and drawing oils, textile auxiliaries and cosmetics.

One method of producing branched fatty acids and esters thereof is based on the Guerbet reaction [Soap, Cosm. Chem. Spec., 52, (1987)] which, by dimerization of alcohols, gives beta-branched alcohols which in turn can be reacted by oxidation to form alpha-branched acids. However, this process involved considerable preparative effort.

A well-known process for the production of branched fatty acids is based on the thermal treatment of unsaturated fatty acids, more particularly tall oil fatty acid, with montmorillonite and water or homogeneous ruthenium catalysts [Fette, Seifen, Anstrichm., 72, 667 (1970), J. Am. Oil. Chem. Soc., 56, 782 (1979), Rev. Fr. Corps, Gras 33, 431 (1986)]. However, the reaction mixture obtained in this process essentially contains high molecular weight dimeric, trimeric and tetrameric fatty acids while the percentage content of branched monomeric fatty acids, for example isostearic acid, is comparatively low and can only be removed from the mixture at considerable cost. Accordingly, the dimerization of fatty acids is of only limited value for the economic production of branched fatty acids.

It is known from U.S. Pat. No. 2,361,018 (1944) that drying oils can be activated with activated olefins, for example cyclopentadiene, dicyclopentadiene or indene, to form branched fatty acids which are used in the paint industry. The Diels-Alder and ene reactions of unsaturated fatty acids and other activated olefins, such as for example acrolein, acrylic acid, crotonaldehyde, crotonic acid, maleic anhydride, maleic acid or methyl vinyl ketone, are reported in Fette, Seifen, Anstrichm., 63, 633 (1961) and in Fat Sci. Techn. 90, 1 (1988). The reaction of butadiene with unsaturated fatty acids is described in J. Chem. Soc. Chem. Comm., 7, 251 (1974). According to the teaching of published Japanese patent application JP 53/34708, erucic acid ester can be reacted with ethylene in the presence of tungsten hexachloride and organoaluminium compounds. However, all the processes mentioned above can only be carried out with considerable outlay on equipment.

Finally, a simple process for the production of branched fatty acid esters thereof is known from Fette, Seifen, Anstrichm., 65, 105 (1963). In this process, unsaturated fatty acids are reacted with short-chain $C_{2-4}$ olefins in a diene reaction. However, the process only gives satisfactory yields where ethylene and propylene are used. With increasing chain length both of the unsaturated fatty acids and of the olefin used, the yields obtained are so poor that the process is unsuitable for industrial application.

Accordingly, the problem addressed by the present invention was to provide a process for the production of branched fatty acids and esters thereof which would be free from the disadvantages mentioned above.

The present invention relates to a process for the production of branched fatty acids and esters thereof by reaction of unsaturated fatty acids or esters thereof with aliphatic non-activated olefins in the presence of layer silicates and active carbon.

It has surprisingly been found that the reaction of unsaturated fatty acids with aliphatic non-activated olefins takes place in a short time and gives comparatively high yields. The present invention also includes the observation that the reaction in the presence of layer silicates and active carbon leads to distinctly smaller percentage contents of oligomeric secondary products than might have been expected from the prior art.

In the context of the invention, unsaturated fatty acids are aliphatic linear carboxylic acids containing 16 to 24 carbon atoms and 1 to 5 double bonds. Typical examples are palmitoleic acid, elaidic acid, petroselic acid, linolenic acid, erucic acid, arachidonic acid or clupanodonic acid. By virtue of their ready accessibility, it is preferred to use unsaturated fatty acids containing 1, 2 or 3 double bonds, more particularly oleic acid, 9,12-linoleic acid and 9,11-linoleic acid ("conjuene acid").

As usual in oleochemistry, the unsaturated fatty acids may even be present in the form of technical mixtures of the type formed in the hydrogenation of natural fats and oils, such as for example coriander oil, soybean oil, cottonseed oil, peanut oil, linseed oil, fish oil or beef tallow. Saturated fatty acids may also be present in these mixtures providing they do not make up more than 50% by weight of the fatty acid composition. By virtue of their high content of oleic and linoleic acid, fatty acid mixtures based on rapeseed oil and sunflower oil are preferred.

The unsaturated fatty acids may also be present in the form of their alkyl or glycerol mono-, di- or triesters. Alkyl esters are understood to be esters of the unsaturated fatty acids with aliphatic alcohols containing 1 to 22 carbon atoms and 0, 1, 2 or 3 double bonds. Typical examples are ethyl, n-propyl, i-propyl, n-butyl, pentyl, hexyl, octyl, 2-ethylhexyl, decyl, lauryl, myristyl, cetyl, stearyl, oleyl, elaidyl, petroselinyl, linolyl, linolenyl, behenyl or erucyl esters. However, methyl esters are preferably used.

Aliphatic non-activated olefins are understood to be linear, cyclic or branched $C_{5-20}$ alkenes with a double bond in the alpha position or an internal double bond. Typical examples of such alkenes are pent-1-ene, hex-1-ene, cyclohexene, hept-1-ene, oct-1-ene, cyclooctene, non-1-ene, dec-1-ene, undec-1-ene, dodec-1-ene, cyclodecene, tetradec-1-ene, hexadec-1-ene, octadec-1-ene, eicos-1-ene and their double bond and skeletal isomers. Linear alpha-olefins containing 6 to 18 and, more particularly, 8 to 10 carbon atoms show particularly high reactivity. Accordingly, they are preferably used.

In the context of the invention, layer silicates are understood to be the elements of main groups 1 to 3 of the periodic system which have a crystal lattice with $SiO_4$ tetrahedrons linked in one plane ("layer lattice") [Ullmanns Enzyclopaedie der technischen Chemie, 4th Edition, Vol. 21, 365 (1984)]. Typical examples are tallow $Mg_3[(OH)_2|[Si_4O_{10}]$ and kaolinite $Al_4[(OH)_8|Si_4O_{10}]$. Montmorillonite $Al_2[(OH)_2|Si_4O_{10}]$ has proved to be a particularly effective catalyst and, accordingly, is preferably used.

The molar ratio of saturated fatty acid or ester to olefin is 1:0.5 to 1:5 and preferably 1:1 to 1:3.5. An optimal reaction rate and a low percentage of secondary products are observed where molar ratios of 1:2 to 1:2.75 are used.

The reaction of the unsaturated fatty acids or esters thereof with the olefins is carried out in the presence of 1 to 30% by weight and preferably 3 to 15% by weight layer silicate, based on the starting materials fatty acid or fatty acid ester plus olefin. Particular selectivity for the formation of monomeric branched fatty acids is observed where 5 to 10% by weight layer silicate is used.

The reaction of the unsaturated fatty acids or esters thereof with olefins is carried out in the simultaneous presence of 0.01 to 3% by weight active carbon, based on the starting materials. Particular selectivity for the formation of monomeric branched fatty acids is observed where 0.1 to 1% by weight active carbon is used.

The reaction of the unsaturated fatty acids or esters thereof with olefins in the presence of layer silicates and active carbon is carried out at temperatures of 200° to 280° C. To obtain an optimal reaction rate, it is of advantage to carry out the reaction at 220° to 260° C. It is advisable, particularly where low-boiling olefins are used, to carry out the reaction under autogenous pressure in an autoclave.

The reaction of the unsaturated fatty acids or esters thereof with olefins in the presence of layer silicates and active carbon is carried out over a period of 0.1 to 5 h. The branched fatty acids and esters are obtained in high yields after only 0.25 to 1.5 h, particularly where oct-1-ene and dec-1-ene are used.

On completion of the reaction, the branched fatty acids can be recovered by distillation.

The branched fatty acids are suitable for the production of surface-active agents, for example surfactants, lubricants, rolling and drawing oils, textile auxiliaries and cosmetics.

The following Examples are intended to illustrate the invention.

EXAMPLES

1. Starting materials

A1. Technical sunflower oil fatty acid, Edenor ® SB05, a product of Henkel KGaA

| Iodine value | 130 |
|---|---|
| Average molecular weight | 280 |
| Composition | 6% by weight palmitic acid |
| | 4% by weight stearic acid |
| | 28% by weight oleic acid |
| | 62% by weight linoleic acid |

A2. Technical oleic acid, Edebor ® TiO₅, a product of Henkel KGaA

| Iodine value | 95 |
|---|---|
| Average molecular weight | 280 |
| Composition | 3% by weight myristic acid |
| | 6% by weight palmitic acid |
| | 5% by weight palmitoleic acid |
| | 3% by weight stearic acid |
| | 73% by weight oleic acid |
| | 11% by weight linoleic acid |

A3. Technical sunflower oil

| Iodine value | 131 |
|---|---|
| Average molecular weight | 886 |
| Composition of the fatty acid component | 6% by weight palmitic acid |
| | 4% by weight stearic acid |
| | 28% by weight oleic acid |
| | 62% by weight linoleic acid |

B1. Oct-1-ene (97% by weight), a product of Janssen Chimica

Average molecular weight : 112

B2. Dec-1-ene (96% by weight), a product of Janssen Chimica

Average molecular weight : 140

C. Montmorillonite K 10, a product of Südchemie

D. Active carbon, powdered, highly pure, a product of Merck

EXAMPLES 1 TO 3

General procedure for the reaction of unsaturated fatty acids with olefins

1 Mol fatty acid A1 or A2 and 2 to 2.75 mol olefin B1 or B2 were introduced into a 1 liter stirred autoclave, after which 5 to 10% by weight montmorillonite and 0.1% by weight active carbon, based in each case on the starting materials, were added. The reaction mixture was heated to T=240°–260° C. and stirred for t=0.25–1.5 h. On completion of the reaction, the reaction mixture was cooled to 20° C. and the solids were removed through a nutsch filter.

The filtrate was then distilled in a high vacuum of 40 Pa and at a temperature of 20° to 240° C. First runnings essentially containing excess olefin and oligomerization and isomerization products thereof and small quantities of fatty acid initially distilled over at a vapor temperature of 20° to 195° C. and were discarded. The branched fatty acids were obtained in the form of a light yellow liquid at a vapor temperature of 195° to 240° C. and were separated off. Oligomerized fatty acids remained behind in the sump in the form of a dark brown viscous liquid.

The reaction parameters and the yields obtained after distillation are shown in Table 1.

EXAMPLE 4

Reaction of sunflower oil with oct-1-ene

Examples 1 to 3 were repeated using 886 g (1 mol) sunflower (A3), 924 g (8.25 mol) oct-1-ene, 10% by weight montmorillonite and 0.1% by weight active carbon, based in each case on the starting materials. The reaction was carried out over t=1.5 h at T=260° C.

Distillation was carried out after pressure hydrogenation of the triglycerides in the same way as in Examples 1 to 3.

TABLE 1

Reaction parameters and yields

| Ex. | Fatty acid (ester) | Olefin | Olefin/ mol | Mont./ % by weight | T/ °C. | t/ mins. | Yld./ mol-% |
|---|---|---|---|---|---|---|---|
| 1.1 | A1 | B1 | 2.00 | 5.0 | 260 | 1.50 | 34.2 |
| 1.2 | A1 | B1 | 2.75 | 5.0 | 260 | 1.50 | 40.0 |

TABLE 1-continued

| | | Reaction parameters and yields | | | | | |
|---|---|---|---|---|---|---|---|
| Ex. | Fatty acid (ester) | Olefin | Olefin/ mol | Mont./ % by weight | T/ °C. | t/ mins. | Yld./ mol-% |
| 1.3 | A1 | B1 | 2.00 | 10.0 | 260 | 1.50 | 35.8 |
| 1.4 | A1 | B1 | 2.00 | 10.0 | 240 | 1.50 | 33.3 |
| 1.5 | A1 | B1 | 2.00 | 10.0 | 260 | 0.25 | 27.6 |
| 2. | A1 | B2 | 2.00 | 10.0 | 260 | 1.50 | 31.7 |
| 3.1 | A2 | B1 | 2.00 | 10.0 | 260 | 1.50 | 33.4 |
| 4.1 | A3 | B1 | 2.00 | 10.0 | 260 | 1.50 | 32.1 |

Legend:
Mont. = montmorillonite
Yld. = molar yield of branched fatty acids, based the molar quantity of unsaturated fatty acid or ester used.

What is claimed is:

1. A process for the production of branched fatty acids and esters thereof comprising the steps of
   A) reacting at least one linear unsaturated fatty acid or ester thereof with at least one aliphatic nonactivated olefin in the presence of a catalyst which is a layer silicate which contains an element of main groups 1 to 3 of the periodic table and which has a crystal lattice with $SiO_4$ tetrahedrons linked in one plane, and active carbon; and
   B) isolating at least one branched fatty acid or ester thereof from the resulting reaction mixture.

2. The process of claim 1 wherein the at least one unsaturated fatty acid or ester thereof contains from 16 to 24 carbon atoms and from 1–3 double bonds in the fatty acid component.

3. The process of claim 2 wherein the at least one unsaturated fatty acid or ester thereof is an ester with either a $C_{1-22}$ aliphatic alcohol containing from 0–3 double bonds or glycerol.

4. The process of claim 1 wherein the at least one aliphatic nonactivated olefin contains from 5 to 20 carbon atoms.

5. The process of claim 1 is wherein the layer silicate is montmorillonite.

6. The process of claim 1 wherein the molar ratio of the at least one linear unsaturated fatty acid or ester to the at least one aliphatic nonactivated olefin is from about 1:0.5 to about 1:5.

7. The process of claim 6 wherein said molar ratio is from about 1:1 to about 1:3.5.

8. The process of claim 6 wherein said molar ratio is from about 1:2 to about 1:2.75.

9. The process of claim 1 wherein step A) is carried out in the presence of from about 1 to about 30% by weight of the layer silicate, based on starting materials.

10. The process of claim 9 wherein step A) is carried out in the presence of from about 5 to about 10% by weight of the layer silicate, based on starting materials.

11. The process of claim 1 wherein step A) is carried out in the presence of from about 0.01 to about 3% by weight of active carbon, based on starting materials.

12. The process of claim 11 wherein step A) is carried out in the presence of from about 0.1 to about 1% by weight of active carbon, based on starting materials.

13. The process of claim 1 wherein step A) is carried out at a temperature in the range of from about 200° to about 280° C.

14. The process of claim 13 wherein step A) is carried out at a temperature in the range of from about 220° to about 260° C.

15. The process of claim 13 wherein step A) is carried out over a period of from about 0.1 to about 5 hours.

16. The process of claim 14 wherein step A) is carried out over a period of from about 0.25 to about 1.5 hours.

17. The process of claim 1 wherein the at least one unsaturated fatty acid or ester thereof is a fatty acid mixture from rapeseed oil or sunflower oil.

18. The process of claim 1 wherein the molar ratio of the at least one linear unsaturated fatty acid or ester to the at least one aliphatic nonactivated olefin is about 1:0.5 to about 1:5; from about 1 to about 30% by weight of the layer silicate is present; from about 0.01 to about 3% by weight of active carbon is present, the above percentages by weight based on starting materials; and wherein step A) is carried out at a temperature of from about 200° to about 280° C. for a period of from about 0.1 to about 5 hours.

19. The process of claim 18 wherein said molar ratio is from about 1:1 to about 1:3.5; the at least one unsaturated fatty acid or ester thereof is a fatty acid mixture from rapeseed oil or sunflower oil; from about 5 to about 10% by weight of montmorillonite is present; from about 0.1 to about 1% by weight of active carbon is present; step A) is carried out at a temperature in the range of from about 220° to about 260° C. for a period of from about 0.25 to about 1.5 hours.

20. In a process for the production of branched fatty acids and esters thereof the improvement wherein at least one unsaturated fatty acid or ester thereof is reacted with at least one aliphatic nonactivated olefin in the presence of a catalyst which is a layer silicate which contains an element of main groups 1 to 3 of the periodic table and which has a crystal lattice with $SiO_4$ tetrahedrons linked in one plane, and activated carbon.

* * * * *